(12) United States Patent
Hagino

(10) Patent No.: US 11,484,656 B2
(45) Date of Patent: Nov. 1, 2022

(54) DRUG SOLUTION ADMINISTRATION DEVICE AND METHOD FOR CONTROLLING DRUG SOLUTION ADMINISTRATION DEVICE

(71) Applicant: TERUMO KABUSHIKI KAISHA, Tokyo (JP)

(72) Inventor: Yoshiharu Hagino, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 337 days.

(21) Appl. No.: 16/807,708

(22) Filed: Mar. 3, 2020

(65) Prior Publication Data

US 2020/0197619 A1  Jun. 25, 2020

Related U.S. Application Data

(63) Continuation of application No. PCT/JP2018/028389, filed on Jul. 30, 2018.

(30) Foreign Application Priority Data

Sep. 28, 2017 (JP) .............................. JP2017-189029

(51) Int. Cl.
| | |
|---|---|
| *A61M 5/315* | (2006.01) |
| *A61M 5/31* | (2006.01) |
| *A61M 5/168* | (2006.01) |

(52) U.S. Cl.
CPC .... *A61M 5/31501* (2013.01); *A61M 5/16831* (2013.01); *A61M 5/3148* (2013.01);
(Continued)

(58) Field of Classification Search
CPC .......... A61M 5/31501; A61M 5/16831; A61M 5/3148; A61M 5/31528; A61M 5/31536;
(Continued)

(56) References Cited

U.S. PATENT DOCUMENTS

| | | | |
|---|---|---|---|
| 2005/0020980 A1* | 1/2005 | Inoue | A61M 39/10 604/152 |
| 2012/0192951 A1* | 8/2012 | Yodfat | A61M 5/16831 137/551 |

FOREIGN PATENT DOCUMENTS

| | | |
|---|---|---|
| CN | 101470036 A | 7/2009 |
| CN | 106540351 A | 3/2017 |

(Continued)

OTHER PUBLICATIONS

Office Action dated Aug. 2, 2021 issued in a corresponding Chinese Patent Application No. 201880055291.0, (9 pages).

International Searching Authority, "Written Opinion," issued in connection with International Patent Application No. PCT/JP2018/028389, dated Sep. 11, 2018.

(Continued)

*Primary Examiner* — James D Ponton
(74) *Attorney, Agent, or Firm* — Foley & Lardner LLP

(57) ABSTRACT

A drug solution administration device includes a drug solution reservoir, a drive unit, a rotation detection unit, and a control unit. The control unit counts the number of rotations of the drive unit from when a rotation sensor value reaches a blockage start threshold value until the rotation sensor value reaches a blockage detection threshold value. Further, the control unit determines that a blockage of a flow path has occurred when the rotation sensor value reaches the blockage detection threshold value, and rotates the drive unit in a direction opposite to a direction in which the drug solution is administered based on the counted number of rotations.

8 Claims, 11 Drawing Sheets

(52) U.S. Cl.
CPC ...... *A61M 5/3155* (2013.01); *A61M 5/31528* (2013.01); *A61M 5/31536* (2013.01); *A61M 5/31576* (2013.01); *A61M 2005/16863* (2013.01); *A61M 2205/103* (2013.01)

(58) Field of Classification Search
CPC ............ A61M 5/3155; A61M 5/31576; A61M 2005/16863; A61M 2205/103; A61M 2005/14506; A61M 2205/18; A61M 2205/3306; A61M 2205/3365; A61M 2205/8206; A61M 5/14248; A61M 5/145; A61M 5/14244; A61M 5/172
See application file for complete search history.

(56) References Cited

FOREIGN PATENT DOCUMENTS

| | | |
|---|---|---|
| JP | S61-58665 A | 3/1986 |
| JP | 2002-136594 A | 5/2002 |
| JP | 2008-264140 A | 11/2008 |
| JP | 2009-219637 A | 10/2009 |
| JP | 2012-205929 A | 10/2012 |
| JP | 2017-131675 A | 8/2017 |
| WO | WO-2014/049647 A1 | 4/2014 |
| WO | WO-2015/146276 A1 | 10/2015 |

OTHER PUBLICATIONS

International Searching Authority, "International Search Report," issued in connection with International Patent Application No. PCT/JP2018/028389, dated Sep. 11, 2018.

* cited by examiner

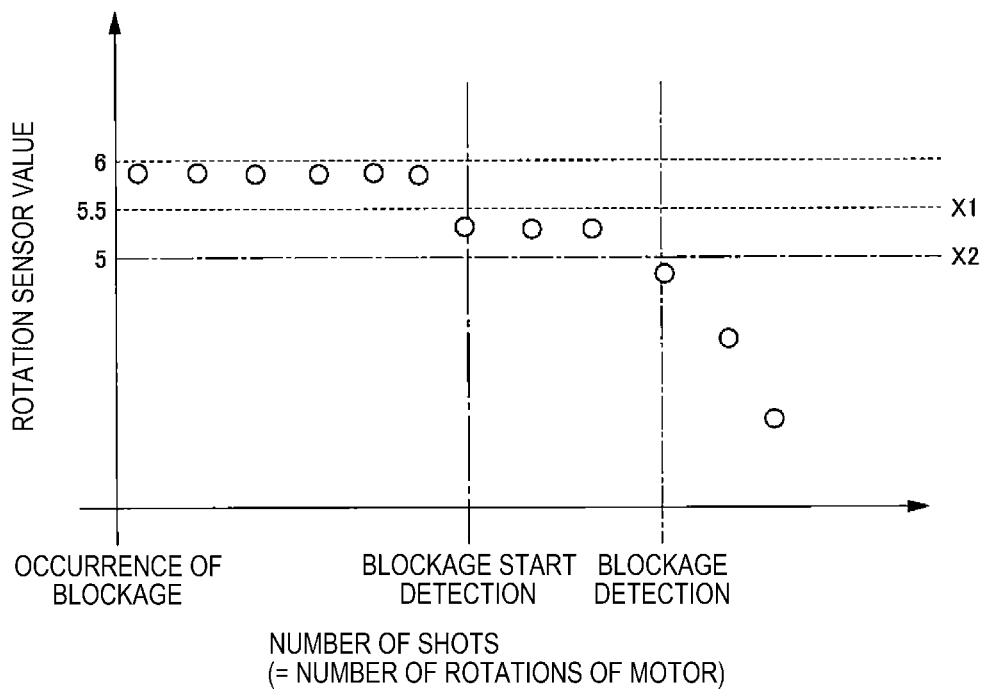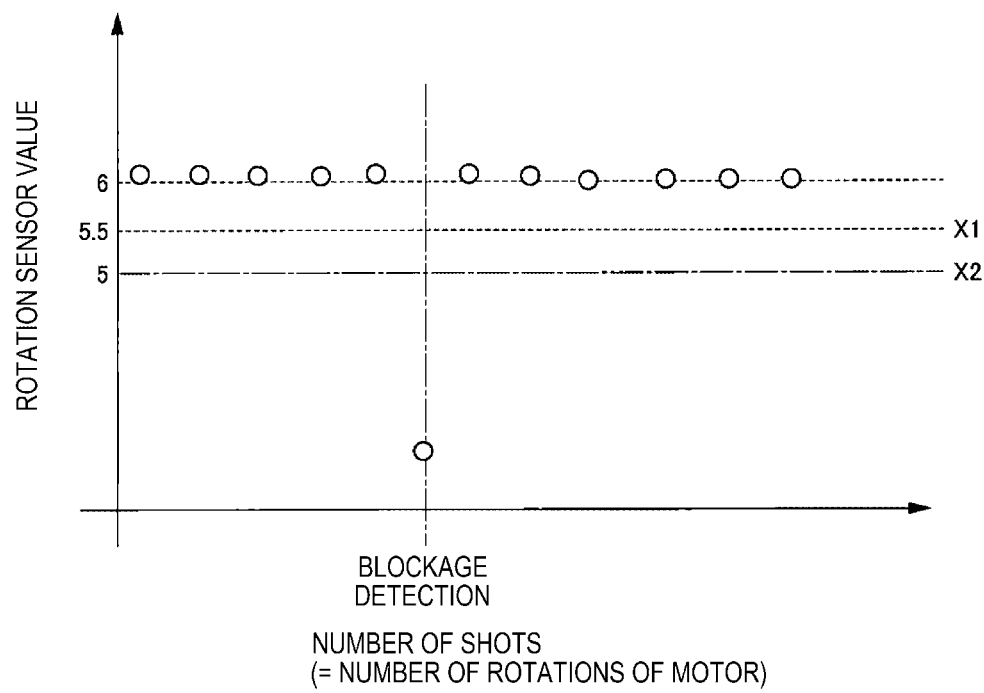

FIG.11

|  | SECOND FROM LAST TIME | LAST TIME | THIS TIME | AVERAGE VALUE |
|---|---|---|---|---|
| PATTERN 1 | 6 | 6 | 2 | (6+6)/2=6 |
| PATTERN 2 | 6 | 4 | 2 | (6+4+2)/3=4 |
| PATTERN 3 | 6 | 6 | 6 | (6+6+6)/3=6 |
| PATTERN 4 | 6 | 2 | 6 | (6+6)/2=6 |

FIG.12

|  | RELATED ART EXAMPLE | EXAMPLE OF PRESENT EMBODIMENT | | | |
|---|---|---|---|---|---|
|  |  | ROTATION SENSOR VALUE | 2-POINT AVERAGE | 3-POINT AVERAGE | 5-POINT AVERAGE |
| AV | 50 | 16.5 | 8.0 | 8.8 | 10.5 |
| MAX | 0 | 26 | 12 | 16.0 | 20 |
| min | 0 | 7 | 3 | 3.0 | 5 |

DRUG SOLUTION ADMINISTRATION DEVICE AND METHOD FOR CONTROLLING DRUG SOLUTION ADMINISTRATION DEVICE

CROSS-REFERENCE TO RELATED APPLICATIONS

This is a bypass continuation of PCT Application No. PCT/JP2018/028389, filed on Jul. 30, 2018, which claims priority to Japanese Application No. 2017-189029, filed on Sep. 28, 2017. The contents of these applications are hereby incorporated by reference in their entireties.

BACKGROUND

The present disclosure relates to a drug solution administration device, and more particularly to a drug solution administration device for performing continuous drug solution administration, such as an insulin pump, and a method for controlling the drug solution administration device.

In recent years, a treatment method in which a drug solution is continuously administered into a patient's body by subcutaneous injection or intravenous injection has been performed. For example, as a treatment method for a diabetic patient, a treatment method in which a minute amount of insulin is continuously injected into the body of the patient has been implemented. In this treatment method, in order to administer a drug solution (insulin) to a patient throughout the day, a portable drug solution administration device (so-called insulin pump) that can be fixedly carried on the patient's body or clothes is used.

As one of such portable drug solution administration devices, a syringe pump type device having a syringe for reserving a drug solution and a plunger driven inside the syringe has been proposed. JP-A-2002-136594 discloses a technique in which a motor indicating a drive unit that operates a plunger and an encoder that detects a change in the rotation speed of the motor are provided. In the technique disclosed in JP-A-2002-136594, blockage of the drug solution flow path is detected from a change in the rotation speed of the motor detected by the encoder.

However, when such a blockage occurs in such a device, the pressure of the drug solution in the flow path increases because the drive unit is driven from the detection of the blockage until the drive of the drive unit is stopped. In this state, because the drug solution with increased pressure is discharged from a liquid feeding pipe when the blocked flow path is opened, there is a possibility that an unintended amount of the drug solution may be administered to the patient when a cannula of a connection port and the liquid feeding pipe are connected. For this reason, in the drug solution administration device of the related art, after the drive of the drive unit is stopped, the drive unit is rotated (reversely rotated) in the direction opposite to the direction in which the drug solution is administered to weaken the pressure of the drug solution in the flow path.

SUMMARY

However, although there are fluctuations in the amount of drug solution fed until the blockage is detected, the drug solution administration device of the related art has a constant number of rotations (number of reverse rotations) for rotating the drive unit in the opposite direction. For this reason, the drug solution administration device of the related art has a problem that the drug solution is discharged unintentionally due to insufficient number of reverse rotations, or body fluid that flows back into the flow path is mixed due to excessive reverse rotation.

In view of the above problems, an object of certain embodiments of the present invention is to provide a drug solution administration device and a method for controlling the drug solution administration device that can appropriately control the number of reverse rotations of the drive unit after detecting a blockage.

According to one embodiment, a drug solution administration device includes a drug solution reservoir, a plunger member, a plunger operation portion, a drive unit, a rotation detection unit, a control unit, and a storage unit.

The drug solution reservoir is filled with a drug solution. The plunger member pushes out the drug solution filled in the drug solution reservoir. The plunger operation portion operates the movement of the plunger member. The drive unit applies a drive force to the plunger operation portion. The rotation detection unit detects a rotation sensor value that is the number of rotations of a rotating body connected to the drive unit when a drive signal for one rotation is output to the drive unit. The control unit detects blockage of the flow path through which the drug solution is sent out based on the rotation sensor value detected by the rotation detection unit, and controls the drive unit. The storage unit stores a blockage detection threshold value, which is a threshold value of the rotation sensor value when the control unit detects blockage and a blockage start threshold value set to a value closer to a normal value of the rotation sensor value detected by the rotation detection unit in a state in which the flow path is not blocked than the blockage detection threshold value.

Then, the control unit counts the number of rotations of the drive unit from when the rotation sensor value reaches the blockage start threshold value until the rotation sensor value reaches the blockage detection threshold value, detects blockage of the flow path when the rotation sensor value reaches the blockage detection threshold value, and rotates the drive unit in a direction opposite to a direction in which the drug solution is administered based on the counted number of rotations.

According to another embodiment, a method for controlling a drug solution administration device includes the following steps (1) to (6).
(1) A step of driving a drive unit to push out a drug solution reserved in a drug solution reservoir via a plunger member.
(2) A step of detecting a rotation sensor value, which is the number of rotations of a rotating body connected to the drive unit by a rotation detection unit when a drive signal for one rotation is output to the drive unit.
(3) A step of determining whether or not the rotation sensor value reaches a blockage detection threshold value.
(4) A step of determining whether or not the rotation sensor value reaches a blockage start threshold value set to a value closer to a normal value of the rotation sensor value detected by the rotation detection unit in a state in which a flow path through which the drug solution is sent out is not blocked than the blockage detection threshold value.
(5) A step of start counting the number of rotations of the drive unit when the rotation sensor value reaches the blockage start threshold value.
(6) A step of detecting blockage of the flow path when the rotation sensor value reaches the blockage detection threshold value and rotating the drive unit in a direction opposite to a direction in which the drug solution is administered based on the counted number of rotations.

According to certain embodiments of the drug solution administration device and the method for controlling the drug solution administration device, it is possible to appropriately control the number of reverse rotations of the drive unit after detecting the blockage.

BRIEF DESCRIPTION OF THE DRAWINGS

FIG. 8 is an explanatory diagram showing a rotation sensor value of the rotation detection unit when blockage occurs in the drug solution administration device according to the exemplary embodiment.

FIG. 9 is an explanatory diagram showing a state in which the rotation sensor value in the drug solution administration device according to the exemplary embodiment falls below the blockage detection threshold value once, that is, a state in which a so-called outlier has occurred.

FIG. 11 is an explanatory diagram showing an example of the rotation sensor value average value calculation process in the drug solution administration device according to the exemplary embodiment.

FIG. 12 is a table showing a comparative example of the number of reverse rotations of the drug solution administration device according to the exemplary embodiment and the number of reverse rotations of the drug solution administration device of the related art.

DETAILED DESCRIPTION

Hereinafter, exemplary embodiments of the drug solution administration device will be described with reference to FIGS. 1 to 13. In each figure, the same reference numbers are used for the same corresponding members. Further, the present invention is not limited to the following embodiments.

1. Exemplary Embodiment

1-1. Configuration of Drug Solution Administration Device

First, an example configuration of a drug solution administration device according to an exemplary embodiment (hereinafter referred to as "present example") will be described with reference to FIGS. 1 to 3.

Figure 1:
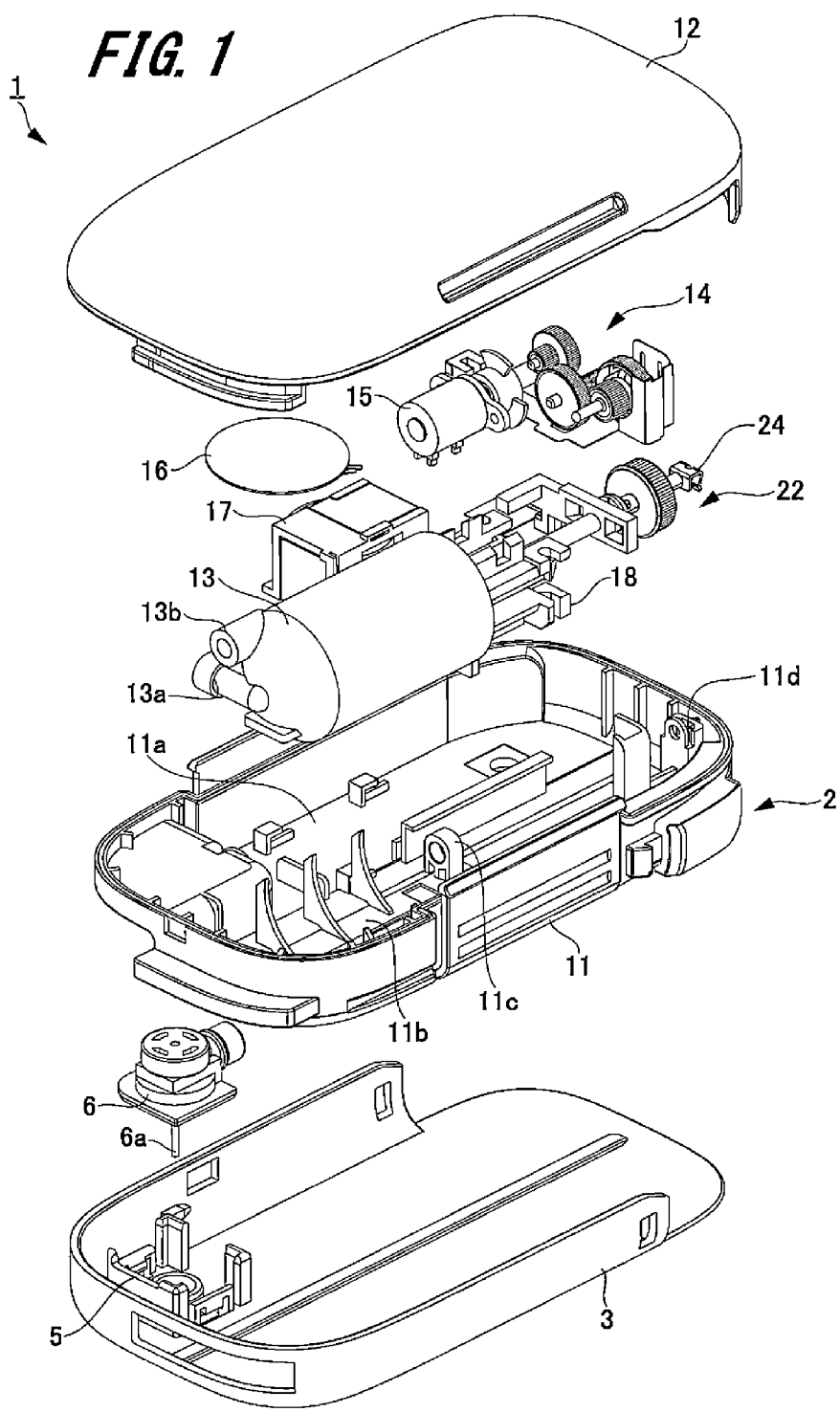
FIG. 1 is an exploded perspective view showing a drug solution administration device according to an exemplary embodiment.
Figure 2:
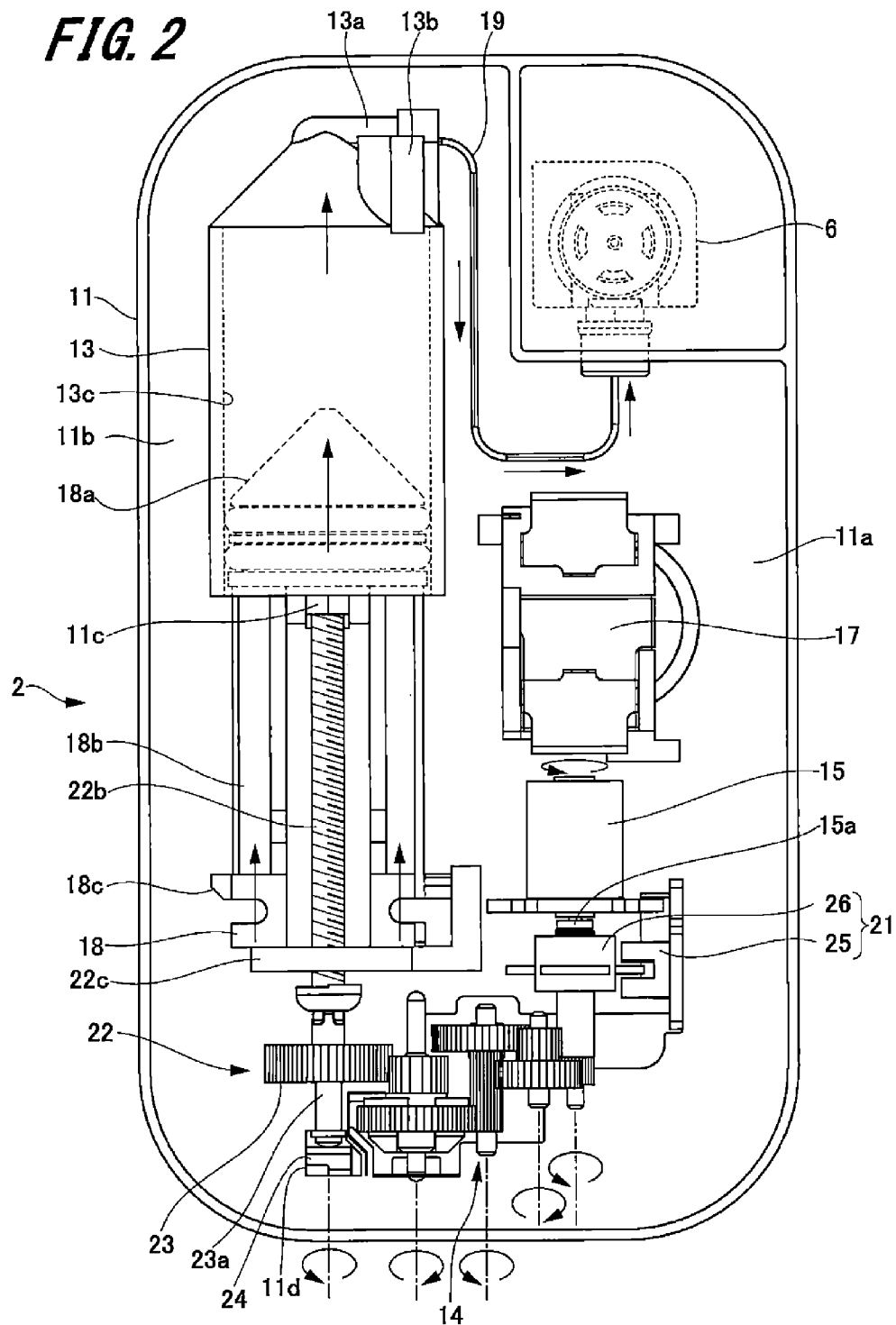
FIG. 2 is a plan view showing the drug solution administration device according to the exemplary embodiment.

FIG. 1 is an exploded perspective view showing a drug solution administration device, and FIG. 2 is a plan view showing the drug solution administration device.

The device shown in FIG. 1 is a portable insulin pump for continuously administering a drug solution into a patient's body, such as a patch-type or tube-type insulin pump, or other portable drug solution administration device. As shown in FIGS. 1 and 2, a drug solution administration device 1 includes a drug solution administration unit 2, a cradle device 3 to which the drug solution administration unit 2 is detachably mounted, and a connection port 6 to be mounted on the cradle device 3.

The cradle device 3 is provided with a mounting portion 5 on which the connection port 6 is mounted. The connection port 6 has a cannula 6a. The connection port 6 is mounted on the mounting portion 5 by attaching the cradle device 3 to the patient's skin and using a puncture mechanism (not shown). When the connection port 6 is mounted on the mounting portion 5 of the cradle device 3, the cannula 6a protrudes from the opposite side of the cradle device 3 on which the drug solution administration unit 2 is mounted, and the cannula 6a is punctured and indwelled in the living body.

Further, the connection port 6 is housed in a back surface housing portion of a casing 11 of the drug solution administration unit 2 when the drug solution administration unit 2 described later is mounted in the state in which the connection port 6 is mounted on the cradle device 3. Then, the connection port 6 is connected to a liquid feeding pipe 19 of the drug solution administration unit 2.

The drug solution administration unit 2 includes the casing 11, a lid 12, a drug solution reservoir 13, a transmission mechanism 14, a drive motor 15 (an example of a drive unit), a reporting unit 16, a power supply unit 17, a plunger member 18 that pushes out the drug solution filled in the drug solution reservoir 13, a liquid feeding pipe 19, a rotation detection unit 21, and a plunger operation portion 22 that operates the plunger member 18.

The casing 11 is formed in a hollow, substantially rectangular parallelepiped shape that is open on one side. The casing 11 is formed with a first housing portion 11a and a second housing portion 11b. The drive motor 15, the power supply unit 17, the rotation detection unit 21, and a part of the transmission mechanism 14 are housed in the first housing portion 11a.

In the second housing portion 11b, the drug solution reservoir 13, the plunger member 18, the plunger operation portion 22, and a part of the transmission mechanism 14 are housed. Further, the second housing portion 11b is provided with a first bearing portion 11c and a second bearing portion 11d. The first bearing portion 11c and the second bearing portion 11d protrude from the bottom portion of the second housing portion 11b toward the opening. A feed screw shaft 22b of a plunger operation portion 22 described later is rotatably supported by the first bearing portion 11c.

A shaft support member 24 is attached to the second bearing portion 11d. Then, a shaft portion 23a of an operation gear 23 in the plunger operation portion 22 described later is rotatably supported by the second bearing portion 11d and the shaft support member 24.

The lid 12 is formed in a substantially flat plate shape. The lid 12 covers the first housing portion 11a and the second housing portion 11b formed in the casing 11, and closes the opening of the casing 11. Further, the transmission mechanism 14, the drive motor 15, the reporting unit 16, the power supply unit 17, and the rotation detection unit 21 are attached to the lid 12.

The drug solution reservoir 13 is formed in a cylindrical shape in which a first end in the axial direction is closed and a second end in the axial direction is opened. The inner diameter of a cylindrical hole 13c in the drug solution reservoir 13 is set to the same size from the opened second end in the axial direction to the closed first end in the axial direction. Therefore, a substantially constant amount of the drug solution is discharged from the drug solution reservoir 13 according to the operation of the plunger member 18. The drug solution is reserved in the cylindrical hole 13c of the drug solution reservoir 13. A liquid feeding port 13a and a filling port 13b are formed at a first end portion of the drug solution reservoir 13 in the axial direction.

The liquid feeding port 13a is connected to the liquid feeding pipe 19. The end portion of the liquid feeding pipe 19 opposite to the liquid feeding port 13a is connected to the connection port 6. The connection port 6 is punctured and indwelled in the patient's living body. Then, the drug solution reserved in the cylindrical hole 13c of the drug solution reservoir is discharged from the liquid feeding port 13a and is administered to the patient through the liquid feeding pipe 19 and the connection port 6.

A filling device (not shown) is connected to the filling port 13b. Then, the drug solution is filled into the cylindrical hole of the drug solution reservoir 13 via the filling port 13b.

Further, a plunger member 18 is slidably inserted into the cylindrical hole 13c of the drug solution reservoir 13. The plunger member 18 has a gasket 18a at the distal end portion and a shaft portion 18b at the rear end portion. The gasket 18a is slidably disposed in the cylindrical hole 13c of the drug solution reservoir 13. The gasket 18a moves while being in liquid tight contact with the inner peripheral surface of the cylindrical hole 13c of the drug solution reservoir 13.

The shape of the distal end portion of the gasket 18a is formed to correspond to the shape of a first end of the cylindrical hole 13c of the drug solution reservoir 13 in the axial direction. Thereby, when the gasket 18a moves to a first end in the axial direction of the drug solution reservoir 13, the drug solution filled in the drug solution reservoir 13 can be discharged from the liquid feeding port 13a without waste.

The shaft portion 18b is provided on the rear end side of the plunger member 18 opposite to the gasket 18a. The shaft portion 18b extends outward from an opening formed at the second end of the drug solution reservoir 13 in the axial direction. An interlock portion 18c that is interlocked to an interlocking nut 22c of the plunger operation portion 22 described later is provided on the rear end side of the shaft portion 18b. When the interlock portion 18c is interlocked to the interlocking nut 22c and the plunger operation portion 22 is driven, the plunger member 18 moves along the axial direction of the drug solution reservoir 13.

The plunger operation portion 22 includes the operation gear 23, the feed screw shaft 22b, and the interlocking nut 22c. The operation gear 23 meshes with a gear of the transmission mechanism 14 described later. Further, a first end of the shaft portion 23a of the operation gear 23 is connected to the rear end side of the feed screw shaft 22b in the axial direction. Furthermore, the second end of the shaft portion 23a of the operation gear 23 is rotatably supported by the second bearing portion 11d and the shaft support member 24.

The feed screw shaft 22b is rotatably supported by the first bearing portion 11c. Further, the feed screw shaft 22b is disposed so that its axial direction is parallel to the shaft portion 18b. That is, the feed screw shaft 22b is arranged in parallel with the moving direction of the plunger member 18. The interlocking nut 22c is screwed to the feed screw shaft 22b.

When the interlocking nut 22c is housed in the casing 11, the rotation of the feed screw shaft 22b around the circumferential direction is restricted. Thereby, when the operation gear 23 rotates and the feed screw shaft 22b rotates, the interlocking nut 22c moves along the axial direction of the feed screw shaft 22b. Then, when the interlock portion 18c of the plunger member 18 is engaged with the interlocking nut 22c, the plunger member 18 moves along the axial direction of the feed screw shaft 22b together with the interlocking nut 22c. Further, the drive force of the drive motor 15 is transmitted to the plunger operation portion 22 via the transmission mechanism 14.

As the drive motor 15, for example, a stepping motor is applied. The drive motor 15 is connected to an electrode of the power supply unit 17 housed in the casing 11 and supplied with electric power in a state in which the opening of the casing 11 is closed with the lid 12. A drive shaft 15a of the drive motor 15 is provided with a rotation detection unit 21 that detects the rotation of the drive shaft 15a.

Figure 3:
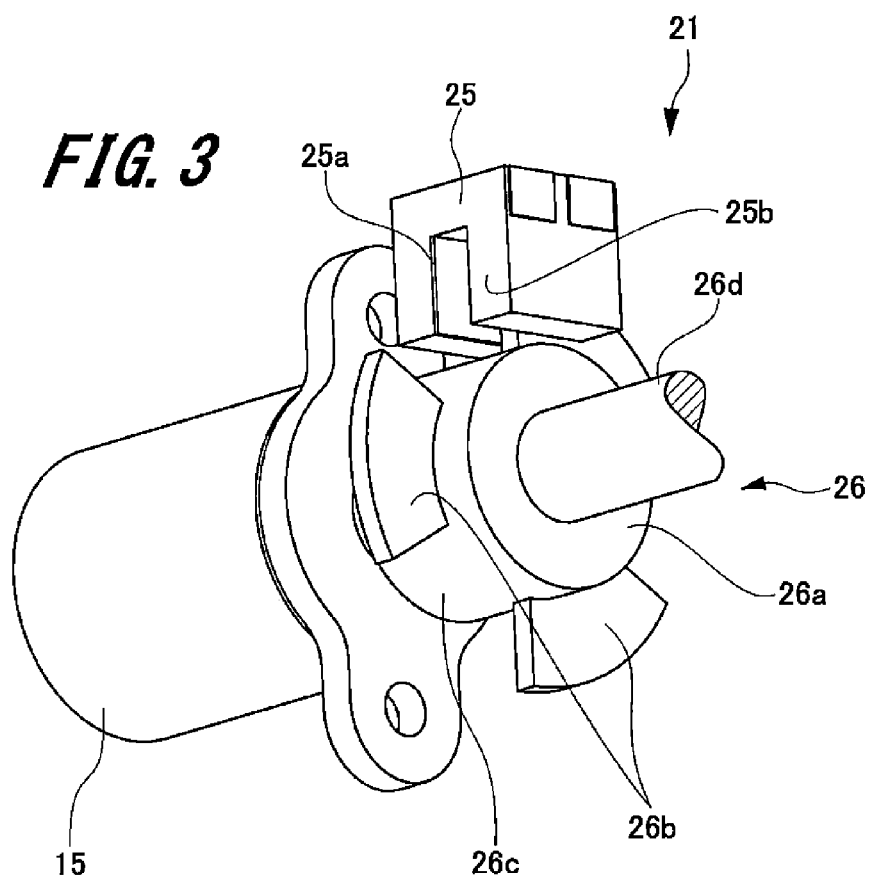
FIG. 3 is a perspective view showing a rotation detection unit in the drug solution administration device according to the exemplary embodiment.

FIG. 3 is a perspective view showing the rotation detection unit 21.

As shown in FIG. 3, the rotation detection unit 21 is a rotary encoder having a detection sensor 25 and a rotating body 26. The rotating body 26 includes a rotating body main body portion 26a fixed to the drive shaft 15a of the drive motor 15, three shielding plates 26b provided on the rotating body main body portion 26a, and a shaft portion 26d provided on the rotating body main body portion 26a.

The rotating body main body portion 26a is formed in a substantially cylindrical shape. Then, the rotating body main body portion 26a rotates in synchronization with the rotation of the drive shaft 15a. The shaft portion 26d protrudes on the opposite side of the rotating body main body portion 26a from the drive shaft 15a in the axial direction. The shaft portion 26d is provided with a gear (not shown) and meshes with the gear of the transmission mechanism 14.

Further, the three shielding plates 26b are provided at equal angular intervals on the outer peripheral surface of the rotating body main body portion 26a. Therefore, three slits 26c are formed at equal angular intervals by the three shielding plates 26b on the periphery of the rotating body main body portion 26a.

The detection sensor 25 is disposed in the casing 11. The detection sensor 25 is an optical sensor having a light emitting unit 25a that emits light and a light receiving unit 25b that receives the light emitted from the light emitting unit 25a. The light emitted from the light emitting unit 25a is blocked by the shielding plate 26b of the rotating body 26 or passes through the slit 26c of the rotating body 26.

As described above, the rotating body 26 is formed with the three shielding plates 26b and the three slits 26c. Therefore, when the drive shaft 15a of the drive motor 15 rotates once, that is, the rotating body 26 rotates one time, a "dark" state in which light is blocked by the shielding plate 26b and a "bright" state in which light passing through the slit 26c is detected change six times in the light receiving unit 25b of the detection sensor 25. Then, the detection sensor 25 detects a pulse signal in which "bright" and "dark" are repeated three times when the rotating body 26 makes one rotation. Thereby, the detection sensor 25 detects the rotation of the rotating body 26.

The number of shielding plates 26b is not limited to three, but may be two, or four or more. Therefore, the pulse signal generated when the rotating body 26 rotates once changes appropriately according to the number of shielding plates 26b and slits 26c.

Further, the detection sensor 25 outputs to a calculation unit 101 rotation information (hereafter referred to as "rotation sensor value") related to the number of rotations of the rotating body 26 when a drive signal of one rotation is output from the calculation unit 101 to the drive motor 15.

The reporting unit 16 is connected to the calculation unit 101 described later. The reporting unit 16 is driven by an instruction from the calculation unit 101 when a malfunction occurs in the drug solution administration device 1 or when blockage is detected, and outputs an alarm. As the alarm output by the reporting unit 16, for example, vibration or sound may be emitted alone, or vibration or sound may be emitted in combination.

The power supply unit 17 is for supplying electric power to each component constituting the drug solution administration device 1. The power supply unit 17 includes, for example, a battery 17a, a battery box that houses the battery 17a, and a switch that turns on/off the supply of electric power from the battery.

1-2. Control System of Drug Solution Administration Device

Next, the control system of the drug solution administration device 1 will be described with reference to FIG. 4.

Figure 4:
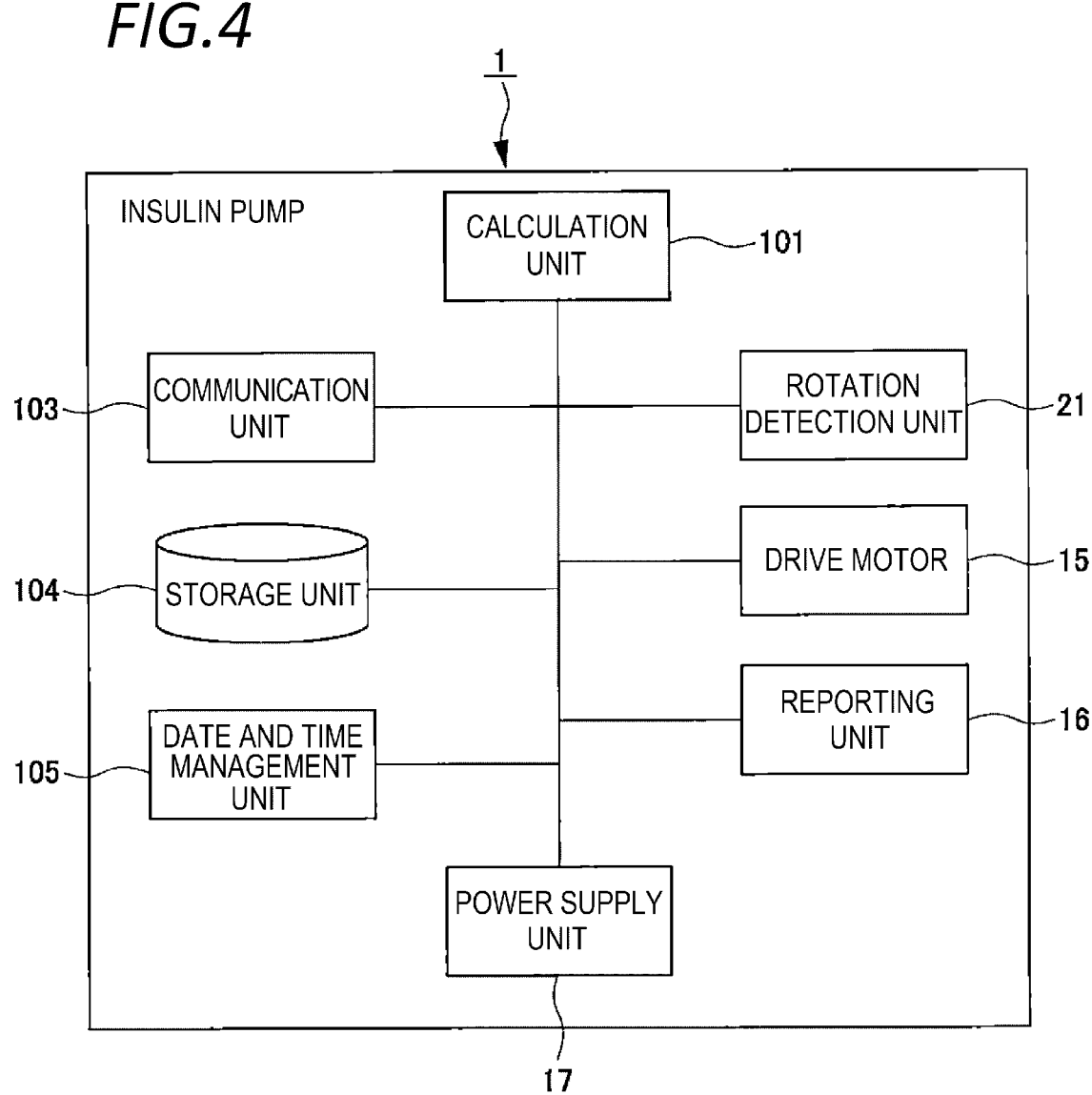
FIG. 4 is a block diagram showing a control system of the drug solution administration device according to the exemplary embodiment.

FIG. 4 is a block diagram showing a control system of the drug solution administration device 1.

As shown in FIG. 4, the drug solution administration device 1 includes the drive motor 15, the rotation detection unit 21, the reporting unit 16, and the power supply unit 17 described above. Further, the drug solution administration device 1 includes the calculation unit 101, which is an example of a control unit, a communication unit 103, a storage unit 104, and a date and time management unit 105.

The drive motor 15, the rotation detection unit 21, the reporting unit 16, the power supply unit 17, the communication unit 103, the storage unit 104, and the date and time management unit 105 are connected to the calculation unit 101.

The rotation sensor value detected by the detection sensor 25 (see FIGS. 1 and 3) of the rotation detection unit 21 is output to the calculation unit 101. Then, the drive of the drive motor 15 is controlled by the calculation unit 101.

The communication unit 103 is connected to a controller (not shown) that operates the drug solution administration device 1, an external portable information processing terminal, and a personal computer (PC) via a wired or wireless network. The communication unit 103 receives operation information on the operation of a user via a controller (not shown), a portable information processing terminal, or the like, or measurement data measured by an external device. Then, the communication unit 103 outputs the received operation information and measurement data to the calculation unit 101.

Further, the communication unit 103 is controlled by the calculation unit 101 to output blockage information, information on the amount of the drug solution reserved in the drug solution reservoir 13, and various types of information about the drug solution administration device 1 such as an administration pattern to a controller (not shown), a portable information processing terminal, or the like.

The storage unit 104 is a part that stores various data. The storage unit 104 stores a control program for controlling an administration profile indicating an administration pattern for administering the drug solution. Further, the storage unit 104 stores a blockage start threshold value $x_1$ and a blockage detection threshold value $x_2$ as threshold values used for blockage detection. The blockage start threshold value $x_1$ and the blockage detection threshold value $x_2$ are threshold values of the rotation sensor value detected by the rotation detection unit 21 or the average value of the rotation sensor values. The blockage start threshold value $x_1$ is set in a range narrower than the blockage detection threshold value $x_2$.

Furthermore, the storage unit 104 stores information received by the communication unit 103, a rotation sensor value detected by the rotation detection unit 21, a reverse rotation counter that counts the number of rotations when the drive motor 15 rotates reversely, and the like. Then, the storage unit 104 outputs a control program stored in advance, a rotation sensor value received from another processing unit, an average value of rotation sensor values, and the like to the calculation unit 101.

The date and time management unit 105 is a program part for performing date and time management, may be installed in a general microcomputer, and outputs date and time information based on a command from the calculation unit 101. This date and time management unit 105 is supplied with electric power even when the power is off so that the date and time management unit 150 outputs accurate date and time information.

The calculation unit 101 is loaded with programs for controlling various devices such as the drive motor 15, the communication unit 103, the storage unit 104, the date and time management unit 105, and the like. Then, the calculation unit 101 controls various operations of the drug solution administration device 1 based on the program. Further, in the calculation unit 101, the rotation detection unit 21 receives the rotation sensor value. Furthermore, the calculation unit 101 calculates an average value of the received rotation sensor values. Then, the calculation unit 101 stores the received information and the calculated average value of the rotation sensor values in the storage unit 104. The rotation sensor value average value calculation process in the calculation unit 101 will be described later.

Further, the calculation unit 101 determines whether or not the flow path of the drug solution is blocked based on the received rotation sensor value and the average value of the rotation sensor values, and counts the number of rotations of the drive motor 15. Further, when the blockage is detected, the calculation unit 101 stops the drive of the drive motor 15 and performs so-called reverse rotation in which the drive motor 15 is rotated by the number of rotations counted in the direction opposite to the direction in which the drug solution is administered. Furthermore, the calculation unit 101 sets the reverse rotation number of the drive motor 15 based on the rotation sensor value and the average value of the rotation sensor values.

The calculation unit 101 drives the drive motor 15 based on the administration profile indicating the administration pattern of the drug solution stored in the storage unit 104. Thereby, the user is administered with a drug solution based on a predetermined administration profile. The calculation unit 101 includes, for example, a central processing unit (CPU), a random access memory (RAM), and a read only memory (ROM), not shown here. The storage unit 104 may be a read only memory (ROM).

1-3. Relationship Between Blockage and Rotation Sensor Value

Figure 5A:
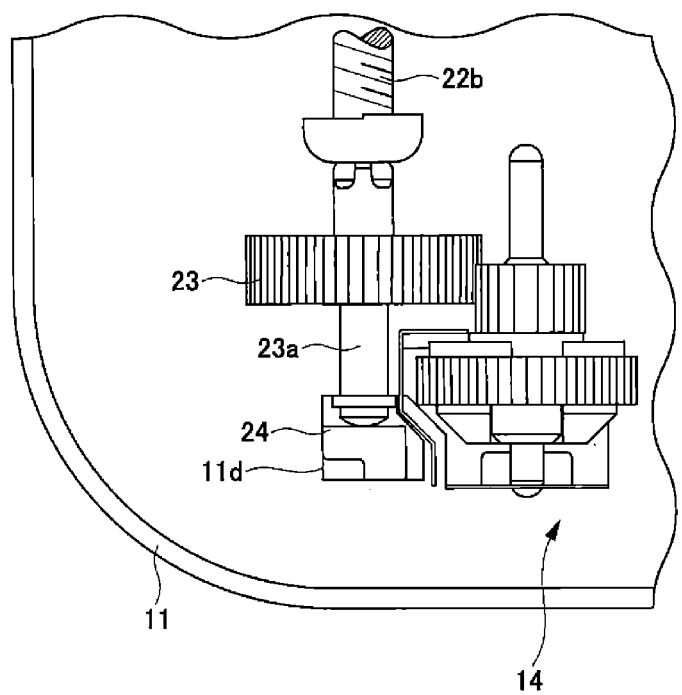
FIGS. 5A and 5B show a state of occurrence of blockage in the drug solution administration device according to the exemplary embodiment, FIG. 5A being an explanatory diagram showing a state before the blockage occurs, and FIG. 5B being an explanatory diagram showing a state in which the blockage occurs.
Figure 5B:
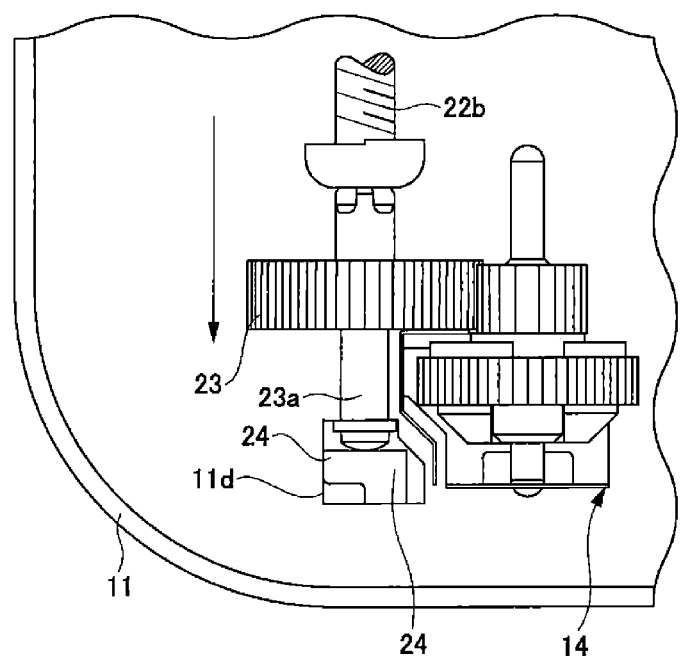
Figure 6:
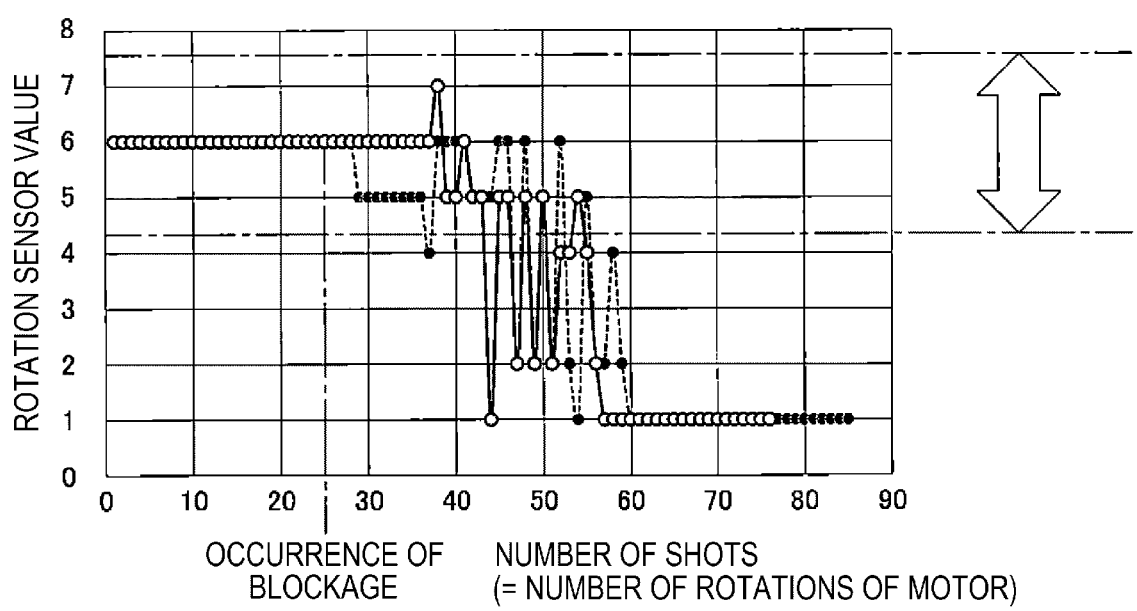
FIG. 6 is an explanatory diagram showing a rotation sensor value of a rotation detection unit when blockage is detected in the drug solution administration device according to the exemplary embodiment.

FIGS. 5A and 5B are plan views showing the periphery of the operation gear 23. Further, FIG. 5A shows a state before the blockage occurs, and FIG. 5B shows a state in which the blockage occurs. FIG. 6 is a graph showing a rotation sensor value in a state in which a blockage has occurred.

As shown in FIG. 5A, in a state in which the drug solution flow path such as the cannula 6a and the liquid feeding pipe 19 (see FIGS. 1 and 2) is not blocked, the operation gear 23 and the second bearing portion 11d are disposed at the normal initial positions shown in FIG. 5A. On the other hand, when blockage occurs in the flow path of the drug solution, the gasket 18a (see FIGS. 1 and 2) is subjected to a drag force in a direction opposite to the direction of pushing out from the drug solution according to the law of action and reaction.

The drag force applied to the gasket 18a is transmitted to the interlocking nut 22c of the plunger operation portion 22 via the shaft portion 18b. As the drag force is transmitted to the interlocking nut 22c, the feed screw shaft 22b, which is screwed with the interlocking nut 22c, is subjected to a drag force in a direction away from the drug solution reservoir 13, that is, toward the rear end side of the shaft portion 18b in the axial direction via the interlocking nut 22c.

Therefore, as shown in FIG. 5B, the shaft portion 23a of the operation gear 23 is also subjected to a drag force in a direction away from the drug solution reservoir 13, that is, toward the second end side in the axial direction, via the feed screw shaft 22b. Then, the second bearing portion 11d and the shaft support member 24 that support the operation gear 23 bend in a direction away from the drug solution reservoir 13. Therefore, the rotation resistance of the operation gear 23 increases due to the drag force when the blockage occurs, and the rotation of the operation gear 23 stops after the second bearing portion 11d and the shaft support member 24 are fully bent. Further, the number of rotations from the occurrence of the blockage until the rotation of the operation gear 23 stops changes according to the degree of bending of the second bearing portion 11d and the shaft support member 24.

Furthermore, the rotation resistance of the operation gear 23 also changes until the second bearing portion 11d and the shaft support member 24 are subjected to a drag force and are fully bent. Therefore, as shown in FIG. 6, in the state in which the blockage does not occur, the number of rotations of the rotating body 26 when the calculation unit 101 outputs a drive signal (number of shots) for rotating the drive motor 15 once is one time, the rotation sensor value detected by the rotation detection unit 21 is "6" (pulse signal in which "bright" and "dark" are repeated three times). Further, when the blockage occurs, the number of rotations of the rotating body 26 fluctuates with respect to the number of shots. Therefore, the rotation sensor value detected by the rotation detection unit 21 is displaced from "6," which is a normal value. Eventually, the rotation of the operation gear 23 stops due to the drag force of the blockage, so that the rotation sensor value converges to "1".

2. Blockage Detection Operation of Drug Solution Administration Device

2-1. Blockage Detection Operation Example

Next, a first operation example of the blockage detection operation at the time of drug solution administration in the drug solution administration device 1 having the above-described configuration will be described with reference to FIGS. 7 to 9.

Figure 7:
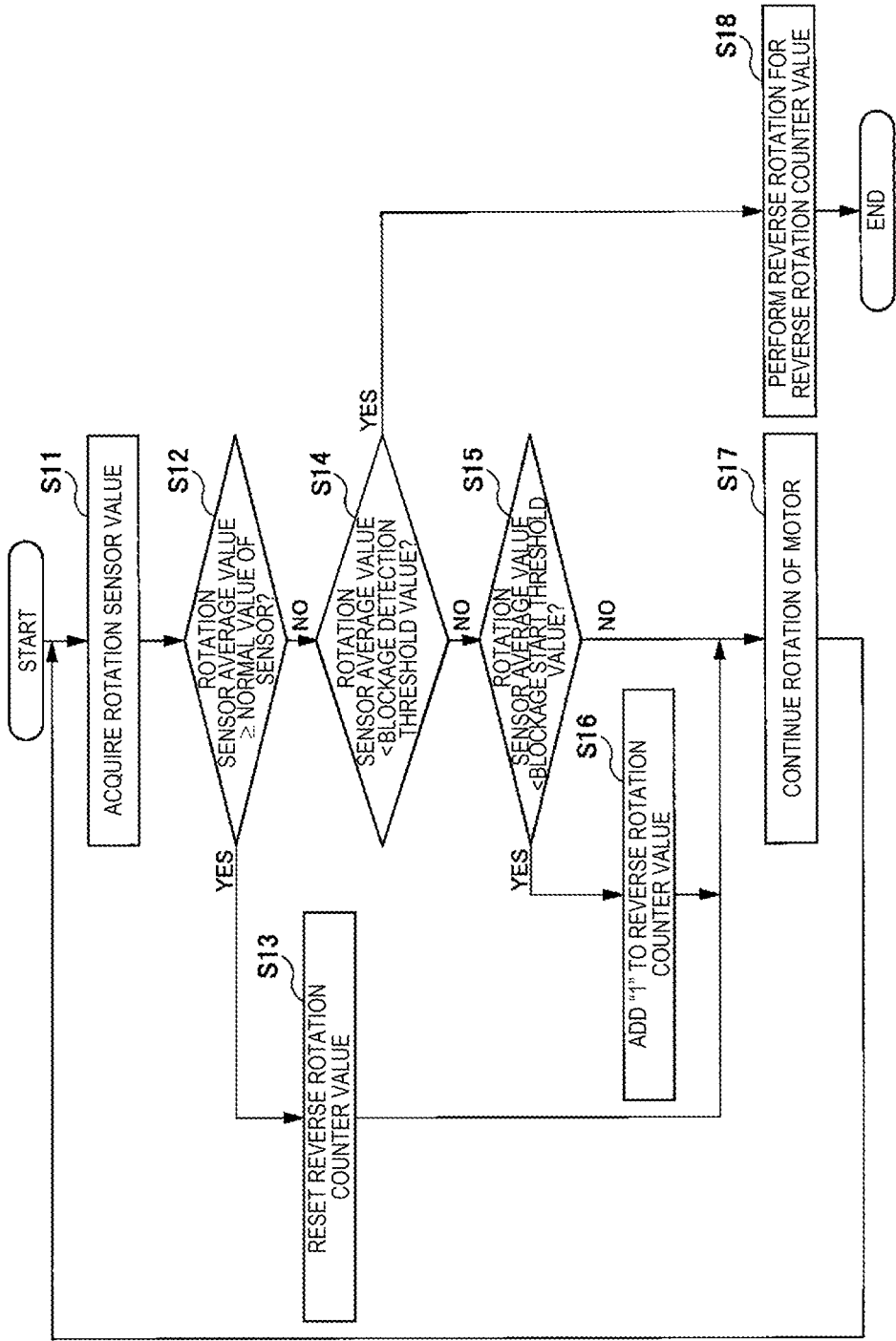
FIG. 7 is a flowchart showing a blockage detection operation in the drug solution administration device according to the exemplary embodiment.

FIG. 7 is a flowchart showing an example of the blockage detection operation, and FIG. 8 is a graph showing the rotation sensor value when the blockage occurs. FIG. 9 is a graph of the rotation sensor value showing a state (outlier) in which the rotation sensor value falls below the blockage detection threshold value $x_2$ once.

The storage unit 104 stores a blockage start threshold value $x_1$ and a blockage detection threshold value $x_2$ in advance. The blockage start threshold value $x_1$ is a rotation sensor value threshold value used when the calculation unit 101 counts the number of reverse rotations. The blockage detection threshold value $x_2$ is a threshold value of a rotation sensor value that the calculation unit 101 determines that a blockage has occurred in the flow path. First, the calculation unit 101 controls the drive motor 15 to rotate the drive motor 15. Next, the calculation unit 101 acquires a rotation sensor value from the rotation detection unit 21 when outputting the number of shots (step S11). Then, the calculation unit 101 calculates an average value of the acquired rotation sensor values.

Next, the calculation unit 101 determines whether or not the average value of the rotation sensor values is a normal value "6" or more (step S12). In the process of step S12, when the calculation unit 101 determines that the average value of the rotation sensor values is a normal value "6" or more (YES determination in step S12), the calculation unit 101 resets the value of the reverse rotation counter stored in the storage unit 104, that is, "0" (step S13). Then, the calculation unit 101 continues the rotational drive of the drive motor 15 (step S17).

On the other hand, in the process of step S12, when the calculation unit 101 determines that the average value of the rotation sensor values is less than the normal value "6" (NO determination in step S12), the calculation unit 101 determines whether or not the average value of the rotation sensor values is less than the blockage detection threshold value $x_2$ (in this example, "5") (step S14). In the process of step S14, when the calculation unit 101 determines that the average value of the rotation sensor values is not less than the blockage detection threshold value $x_2$ (NO determination in step S14), the calculation unit 101 determines whether or not the average value of the rotation sensor values is less than the blockage start threshold value $x_1$ (in present example, "5.5") (step S15)

In the process of step S15, when the calculation unit 101 determines that the average value of the rotation sensor values is not less than the blockage start threshold value $x_1$ (NO determination in step S15), the rotation drive of the drive motor 15 is continued (step S17). Then, the process returns to step S11.

On the other hand, in the process of step S15, as shown in FIG. 8, when the calculation unit 101 determines that the average value of the rotation sensor values is less than the blockage start threshold value $x_1$ (YES determination in step S15), the calculation unit 101 detects that the blockage has started. Then, the calculation unit 101 adds "1" to the value of the reverse rotation counter stored in the storage unit 104 (step S16). The calculation unit 101 continues the rotational drive of the drive motor 15 (step S17). Then, the calculation unit 101 returns to the process of step S11.

Further, in the process of step S14, as shown in FIG. 8, when the calculation unit 101 determines that the average value of the rotation sensor values is less than the blockage detection threshold value $x_2$ (YES determination in step S14), the calculation unit 101 detects a blockage. Then, the calculation unit 101 reversely rotates the drive motor 15 by the number of reverse rotation counters stored in the storage unit 104 in the process of step S16 (step S18). By performing the above-described steps, the blockage detection operation of the drug solution administration device 1 is completed.

At this time, in the process of step S18, the number of reverse rotation counters that perform reverse rotation is the number of rotations from the average value of the rotation sensor values below the blockage start threshold value $x_1$ to the blockage detection threshold value $x_2$. However, an additional calculation may be performed in order to reduce a calculation error from when the blockage occurs until it falls below the blockage start threshold value $x_1$. For example, by adding a certain number (such as 1) to the number of reverse rotation counters, or by adding a pre-calculated number of rotations based on the numerical value according to the inspection value at the time of production in advance, the number of reverse rotations can be made close to the actual number of reverse rotations after the blockage. When using the average value of the rotation sensor values, it is possible to set the blockage start threshold value $x_1$ finely, similarly, the calculation error can be reduced by reducing the difference between the rotation sensor value and the normal value.

Thus, according to the drug solution administration device 1 of the present example, the number of rotations of the drive motor 15 from when the blockage is started until the calculation unit 101 detects the blockage can be counted by providing a blockage detection threshold value $x_2$ and a blockage start threshold value $x_1$ that is closer to the normal value of the rotation sensor value than the blockage detection threshold value $x_2$. Thereby, the number of reverse rotations of the drive motor 15 can be controlled to an appropriate number of rotations. As a result, it is possible to prevent body fluid that flowed backward into the flow path due to excessive reverse rotation from being mixed or prevent the drug solution from being discharged unintentionally because the pressure in the flow path cannot be sufficiently reduced due to insufficient number of reverse rotations.

In order to detect blockage early, when the range of the blockage detection threshold value $x_2$ is set narrow, outliers as shown in FIG. 9 are generally detection abnormal values in many cases, and in the case of the setting for determining that the blockage has occurred in the calculation unit 101, erroneous detection in the calculation unit 101 increases.

In order to prevent such erroneous detection, in the present example, by using the average value of the rotation sensor values calculated by the calculation unit 101, the elapsed time until the blockage detection is shortened while preventing the erroneous detection due to the outlier as shown in FIG. 9 described above. Further, instead of using the average value of the rotation sensor values, the calculation unit 101 may determine that a blockage has occurred when the rotation sensor value continuously falls below the blockage detection threshold value $x_2$. Alternatively, the calculation unit 101 may determine that a blockage has occurred when the rotation sensor value is a specified number or more and is less than a blockage detection threshold value $x_2$ while the number of rotations of the drive motor 15 is within a predetermined number of rotations. For example, when the rotation sensor value is m times or more and is less than the blockage detection threshold value $x_2$ while the drive motor 15 rotates n times, the calculation unit 101 determines that a blockage has occurred. The predetermined number of rotations n and the specified number of times m are randomly set. For example, the number of rotations n may be set to 3 times and the specified number of times m may be set to 2 times, or the number of rotations n may be set to 4 times and the specified number of times m may be set to 3 times.

2-2. Rotation Sensor Value Average Value Calculation Process

Next, an example of rotation sensor value average value calculation process will be described with reference to FIGS. 10 and 11. An example in which the detection accuracy can be further improved by excluding the outlier shown in FIG. 9 in the calculation of the average value will be described as follows.

Figure 10:
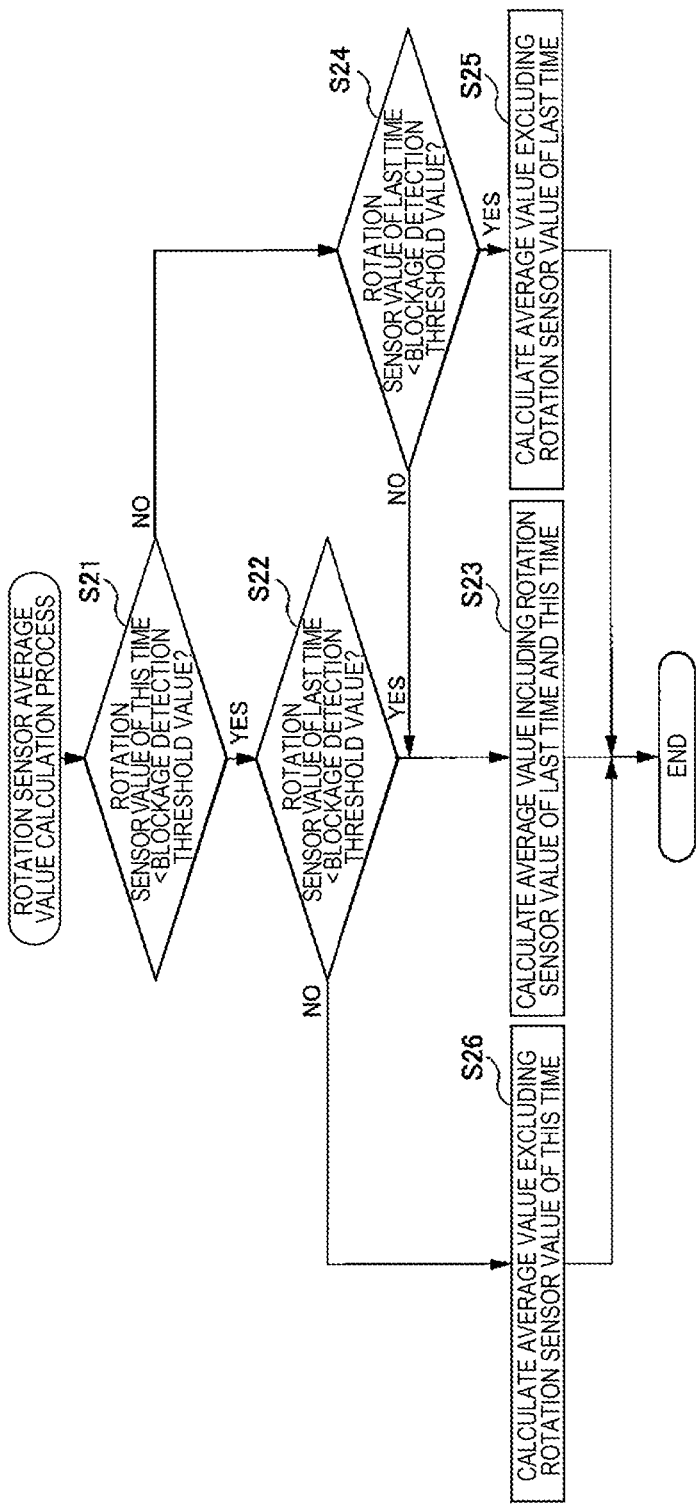
FIG. 10 is a flowchart showing an example of a rotation sensor value average value calculation process in the drug solution administration device according to the exemplary embodiment.

FIG. 10 is a flowchart showing an example of the rotation sensor value average value calculation process, and FIG. 11 is a table showing an example of the rotation sensor value average value calculation process.

As shown in FIG. 10, first, the calculation unit 101 determines whether or not the rotation sensor value acquired this time is less than the blockage detection threshold value $x_2$ (step S21). In step S21, when the calculation unit 101 determines that the rotation sensor value acquired this time is less than the blockage detection threshold value $x_2$ (YES determination in step S21), the calculation unit 101 determines whether or not the rotation sensor value acquired the last time is less than the blockage detection threshold value $x_2$ (step S22).

In step S22, when the calculation unit 101 determines that the rotation sensor value acquired the last time is less than the blockage detection threshold value $x_2$ (YES determination in step S22), the calculation unit 101 calculates the average value of the rotation sensor values including the rotation sensor value acquired the last time and the rotation sensor value acquired this time (step S23). That is, as shown in the pattern 2 shown in FIG. 11, the calculation unit 101 calculates the average value of the rotation sensor values including all the rotation sensor values acquired the second from the last time, the last time, and this time.

Further, in step S21, when the calculation unit 101 determines that the rotation sensor value acquired this time is not less than the blockage detection threshold value $x_2$ (NO determination in step S21), the calculation unit 101 determines whether or not the rotation sensor value acquired the last time is less than the blockage detection threshold value $x_2$ (step S24). In step S24, when the calculation unit 101 determines that the rotation sensor value acquired the last time is not less than the blockage detection threshold value $x_2$ (NO determination in step S24), the calculation unit 101 performs the process of step S23 described above. That is, as shown in the pattern 3 shown in FIG. 11, the calculation unit 101 calculates the average value of the rotation sensor values including all the rotation sensor values acquired the second from the last time, the last time, and this time.

In step S24, when the calculation unit 101 determines that the rotation sensor value acquired the last time is less than the blockage detection threshold value $x_2$ (YES determination in step S24), the calculation unit 101 calculates the average value of the rotation sensor values excluding the rotation sensor value acquired the last time (step S25). That is, as shown in pattern 4 of FIG. 11, the rotation sensor value "2" acquired the last time is excluded, and the calculation unit 101 calculates the average value of the rotation sensor values using the rotation sensor value acquired this time and the rotation sensor value acquired the second from the last time.

Furthermore, when the calculation unit 101 determines in step 22 that the rotation sensor value acquired the last time is not less than the blockage detection threshold value $x_2$ (NO determination in step S22), the calculation unit 101 calculates the average value of the rotation sensor values excluding the rotation sensor value acquired this time (step S26). That is, as shown in pattern 1 of FIG. 11, the rotation sensor value "2" acquired this time is excluded, and the calculation unit 101 calculates the average value of the rotation sensor values using the rotation sensor value acquired the last time and the rotation sensor value acquired the second from the last time. Thereby, the rotation sensor value average value calculation process by the calculation unit 101 is completed.

The process of calculating the average value of the rotation sensor values is not limited to the method of excluding outliers using the threshold value as described above as the blockage detection threshold value $x_2$. For example, it may be average movement value, that is, continuous rotation sensor value data in the present example obtained by continuously calculating an average value from rotation sensor values in randomly continuous periods, or the average value of the rotation sensor value acquired this time and the rotation sensor value until the past predetermined number of times may be calculated without removing the acquired rotation sensor value. Alternatively, the average value of a rotation sensor value may be calculated without using the continuous numerical value in random numbers.

3. Related Art Example and Comparative Example

Next, a comparative example of the reverse rotation speed between the related art example and this example will be described with reference to FIGS. 12 and 13.

Figure 13:
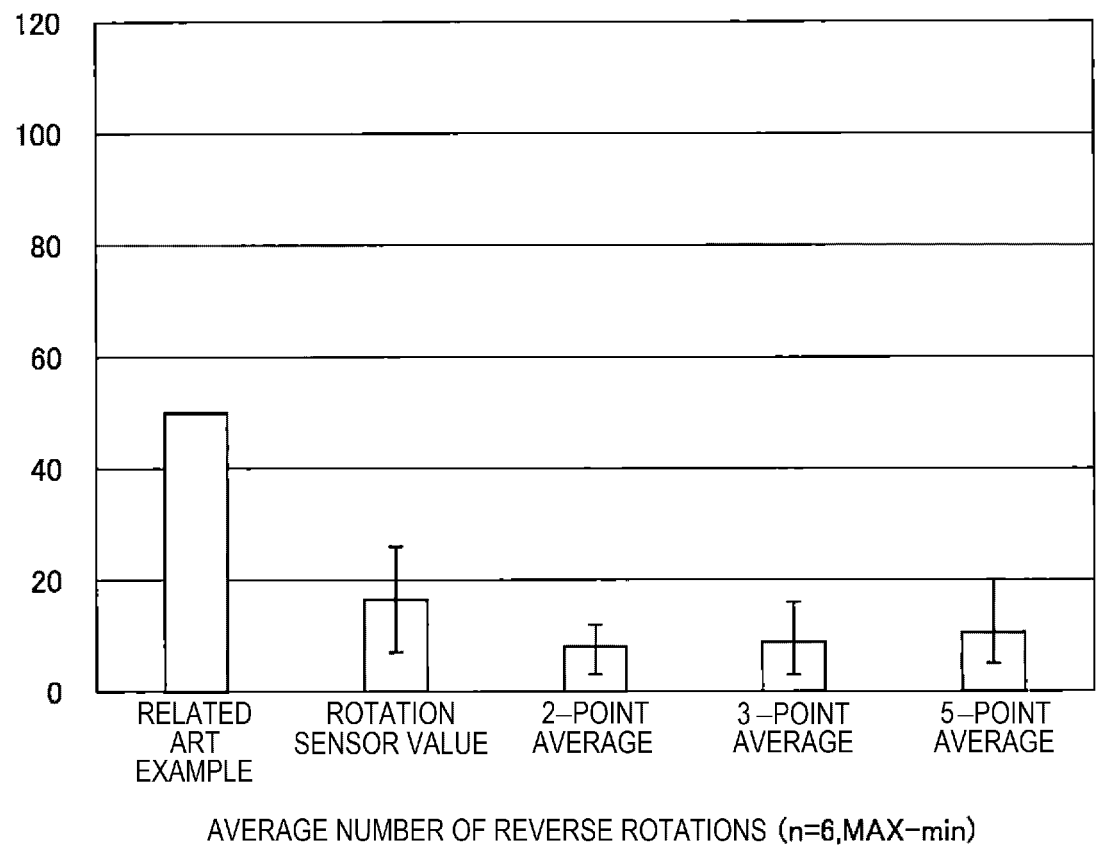
FIG. 13 is a graph showing FIG. 12.

FIG. 12 is a table showing the number of reverse rotations of the related art example and the present example, and FIG. 13 is a graph showing the number of reverse rotations of the related art example and the present example. The value of the reverse rotation speed shown in FIGS. 12 and 13 is an average value when the blockage occurs six times using the same drug solution administration unit 2.

As shown in FIGS. 12 and 13, the number of reverse rotations of the related art example is always constant, for example, 50 times. On the other hand, the reverse rotation speed in the present example is a value obtained by counting the number of rotations of the drive motor 15 from when the rotation sensor value falls below the blockage start threshold value $x_1$ to below the blockage detection threshold value $x_2$.

In the "rotation sensor value" in the present example, it is detected as blockage when the rotation sensor value continuously falls below the blockage detection threshold value $x_2$ without calculating the average value of the rotation sensor values. Further, in the "2-point average", it is detected as blockage when the average value of 2 points of the rotation sensor value acquired this time and the rotation sensor value acquired the last time is less than the blockage detection threshold value $x_2$. In the "3-point average", it is detected as blockage when the average value of the 3 points rotation sensor values of the past continuous values of three times including the rotation sensor value acquired this time is less than the blockage detection threshold value $x_2$. Then, in the "5-point average", it is detected as blocked when the average value of the 5 points rotation sensor values of the past continuous values of five times including the rotation sensor value acquired this time is less than the blockage detection threshold value $x_2$.

As shown in FIGS. 12 and 13, it can be seen that all of the "rotation sensor value", "2-point average", "3-point average", and "5-point average" in the number of reverse rotations of the present example are less than 50 times of reverse rotations of the related art example. Thereby, according to the drug solution administration device of the present example, it can prevent being excessively reversely rotated like the related art example.

Furthermore, as shown in FIGS. 12 and 13, it can be seen that the example in which the average value of the rotation sensor values is calculated has a smaller number of reverse rotations than the "rotation sensor value", which is an example in which the rotation sensor value continuously falls below the blockage detection threshold value $x_2$. The timing to start counting the number of reverse rotations is when the rotation sensor value falls below the blockage start threshold value $x_1$ regardless of whether the rotation sensor value is used or the average value of the rotation sensor values is used. For this reason, the timing of starting counting the number of reverse rotations is the same timing for both the rotation sensor value and the average value of the rotation sensor values.

Therefore, the low number of reverse rotations means that the elapsed time from the time when the number of rotations falls below the blockage start threshold value $x_1$ to the time when it falls below the blockage detection threshold value $x_2$ is small, and the number of rotations of the drive motor 15 is small. In particular, it can be seen that the example using "2-point average" is the shortest. As a result, it can be seen that the detection speed until the calculation unit 101 detects the blockage is improved in the example in which the average value of the rotation sensor values is calculated rather than the example in which the blockage is detected when the rotation sensor value continuously falls below the blockage detection threshold value $x_2$.

As described above, when narrowing the range of the blockage detection threshold value $x_2$ and attempting to perform blockage detection earlier, erroneous detection also increases. On the other hand, by using the average value of the rotation sensor values, it is possible to improve the accuracy of the blockage detection and improve the detection speed. Thereby, the range of the blockage detection threshold value $x_2$ can be narrowed. In the example shown in FIGS. 12 and 13, in the calculation of the average value of the rotation sensor values, the average value calculation process excluding the outlier shown in FIG. 10 is not performed, but the same effect as when the average value calculation process shown in FIG. 10 is performed is shown.

Example embodiments of the present invention and their effects have been described above. However, the drug solution administration device of the present invention is not limited to the above-described embodiments, and various modifications can be made without departing from the spirit of the invention described in the claims.

In the exemplary embodiment described above, the example in which the blockage start threshold value $x_1$ is set to "5.5" and the blockage detection threshold value $x_2$ is set to "5" has been described, but the present invention is not limited to this. The values of the blockage start threshold value $x_1$ and the blockage detection threshold value $x_2$ are appropriately set according to the number of shielding plates 26b of the rotating body 26, the normal value of the rotation sensor value, the required detection accuracy, and the detection speed.

Furthermore, in the blockage detection operation shown in FIG. 7 described above, the example in which it is determined whether the average value of the rotation sensor value in which the calculation unit 101 calculated is less than the blockage start threshold value $x_1$ or the blockage detection threshold value $x_2$ is demonstrated, but the present invention is not limited to this. For example, the rotation sensor value may be used to determine whether or not it is less than the blockage start threshold value $X_1$, and the calculated average value of the rotation sensor values may be used to determine whether or not it is less than the blockage detection threshold value $X_2$. Further, the calculated average value of rotation sensor values may be used to determine whether or not it is less than the blockage start threshold value $X_1$, and a rotation sensor value may be used to determine whether or not it is less than the blockage detection threshold value $X_2$.

Further, the calculation unit 101 may detect the blockage when the rotation sensor value reaches the blockage start threshold value $X_1$. Then, the number of rotations from when the blockage is detected until the drive motor 15 is completely stopped may be counted, and the drive motor 15 may be rotated in the reverse direction by the counted number.

In the above-described exemplary embodiment, the example in which the insulin pump that administers insulin is applied as the drug solution administration device has been described. However, the present invention is not limited to this. As the drug solution to be administered, various other drug solutions such as analgesics, anticancer drugs, HIV drugs, iron chelating drugs, pulmonary hypertension drugs and the like may be used.

REFERENCE SIGNS LIST

1 . . . drug solution administration device
2 . . . drug solution administration unit
3 . . . cradle device
5 . . . mounting portion
6 . . . connection port
6a . . . cannula
11 . . . casing
11c . . . first bearing portion
11d . . . second bearing portion
12 . . . lid
12a . . . one side
13 . . . drug solution reservoir
14 . . . transmission mechanism
15 . . . drive motor (drive unit)
15a . . . drive shaft
16 . . . reporting unit
17 . . . power supply unit
18 . . . plunger member
18a . . . gasket
18b . . . shaft portion
18c . . . interlock portion
19 . . . liquid feeding pipe
21 . . . rotation detection unit
22 . . . plunger operation portion
22b . . . feed screw shaft
22c . . . interlocking nut
23 . . . operation gear
23a . . . shaft portion
24 . . . shaft support member
25 . . . detection sensor
26 . . . rotating body
26a . . . rotating body main body portion
26b . . . shielding plate
26c . . . slit
26d . . . shaft portion
101 . . . calculation unit (control unit)
104 . . . storage unit
$x_1$ . . . blockage start threshold value
$x_2$ . . . blockage detection threshold value

The invention claimed is:

1. A drug solution administration device comprising:
a drug solution reservoir configured to be filled with a drug solution;
a plunger member configured to push out the drug solution filled in the drug solution reservoir;
a plunger operation portion configured to operate movement of the plunger member;
a drive unit configured to apply a drive force to the plunger operation portion;
a rotation detection unit configured to detect a rotation sensor value indicative of a number of rotations of a rotating body connected to the drive unit when a drive signal for one rotation of the rotating body is output to the drive unit;
a control unit configured to determine that a blockage has occurred in a flow path through which the drug solution is sent out based on the rotation sensor value detected by the rotation detection unit, and to control the drive unit; and
a storage unit configured to store:
a blockage detection threshold value, which is a threshold value of the rotation sensor value at which the control unit determines that the blockage has occurred, and
a blockage start threshold value set to a value closer to a normal value of the rotation sensor value detected by the rotation detection unit in a state in which the flow path is not blocked than the blockage detection threshold value,
wherein the control unit is configured to:
count the number of rotations of the rotating body from when the rotation sensor value reaches the blockage start threshold value until the rotation sensor value reaches the blockage detection threshold value,
determine that the blockage of the flow path has occurred when the rotation sensor value reaches the blockage detection threshold value, and
control the drive unit to rotate in a direction opposite to a direction in which the drive unit is rotated when the drug solution is administered, based on the counted number of rotations.

2. The drug solution administration device according to claim 1,
wherein the control unit is configured to determine that the blockage of the flow path has occurred when the rotation sensor value continuously reaches the blockage detection threshold value.

3. The drug solution administration device according to claim 1,
wherein the control unit is configured to determine that the blockage of the flow path has occurred when the rotation sensor value reaches the blockage detection threshold value a specified number of times or more and within a predetermined number of rotations of the drive unit.

4. The drug solution administration device according to claim 1,
wherein the control unit is configured to:
acquire the rotation sensor value a plurality of times from the rotation detection unit,
calculate an average value of the plurality of rotation sensor values, and
determine that the blockage of the flow path has occurred when the calculated average value reaches the blockage detection threshold value.

5. The drug solution administration device according to claim 4,
wherein the control unit is configured to calculate the average value of the rotation sensor values excluding the rotation sensor value reaching the blockage detection threshold value once among the plurality of acquired rotation sensor values.

6. The drug solution administration device according to claim 1,
wherein the control unit is configured to add a certain number or a number of rotations calculated in advance to the counted number of rotations when rotating the drive unit in the opposite direction.

7. A method for controlling a drug solution administration device, the method comprising:
a step of driving a drive unit to push out a drug solution reserved in a drug solution reservoir via a plunger member;
a step of detecting a rotation sensor value indicative of a number of rotations of a rotating body connected to the drive unit by a rotation detection unit when a drive signal for one rotation of the rotating body is output to the drive unit;
a step of determining when the rotation sensor value reaches a blockage start threshold value set to a value closer to a normal value of the rotation sensor value detected by the rotation detection unit in a state in which a flow path through which the drug solution is sent out is not blocked than a blockage detection threshold value;
a step of starting to count a number of rotations of the rotating body when the rotation sensor value reaches the blockage start threshold value; and
a step of determining when the rotation sensor value reaches the blockage detection threshold value;
a step of determining that a blockage of the flow path has occurred when the rotation sensor value reaches the blockage detection threshold value, and rotating the drive unit in a direction opposite to a direction in which the drive unit is rotated when the drug solution is administered, based on the counted number of rotations.

8. A drug solution administration device comprising:
a drug solution reservoir configured to be filled with a drug solution;
a plunger configured to push out the drug solution filled in the drug solution reservoir;
a drive motor configured to drive the plunger, the drive motor comprising a drive shaft;
a rotary encoder comprising:
a rotating body connected to the drive shaft,
and a detection sensor configured to detect a sensor value indicative of a number of rotations of the rotating body when a drive signal for one rotation of the rotating body is output to the drive motor;
a controller configured to determine that a blockage has occurred in a flow path through which the drug solution is sent out based on the rotation sensor value detected by the rotary encoder, and to control the drive motor; and
a memory configured to store:
a blockage detection threshold value, which is a threshold value of the rotation sensor value at which the controller determines that the blockage has occurred, and
a blockage start threshold value set to a value closer to a normal value of the rotation sensor value detected by the rotary encoder in a state in which the flow path is not blocked than the blockage detection threshold value,
wherein the controller is configured to:
count the number of rotations of the rotating body from when the rotation sensor value reaches the blockage start threshold value until the rotation sensor value reaches the blockage detection threshold value,
determine that the blockage of the flow path has occurred when the rotation sensor value reaches the blockage detection threshold value, and
control the drive motor to rotate in a direction opposite to a direction in which the drive motor is rotated when the drug solution is administered, based on the counted number of rotations.

* * * * *